United States Patent
Heuser

(10) Patent No.: US 7,300,459 B2
(45) Date of Patent: Nov. 27, 2007

(54) STENT WITH COVERING AND DIFFERENTIAL DILATION

(76) Inventor: Richard R. Heuser, 500 W. Thomas Rd., Suite 900, Phoenix, AZ (US) 85013

( * ) Notice: Subject to any disclaimer, the term of this patent is extended or adjusted under 35 U.S.C. 154(b) by 0 days.

(21) Appl. No.: 10/687,783

(22) Filed: Oct. 17, 2003

(65) Prior Publication Data

US 2004/0148005 A1 Jul. 29, 2004

Related U.S. Application Data

(60) Provisional application No. 60/419,508, filed on Oct. 17, 2002.

(51) Int. Cl.
*A61F 2/06* (2006.01)
(52) U.S. Cl. .................... 623/1.34; 623/1.44
(58) Field of Classification Search ....... 623/1.11–1.44
See application file for complete search history.

(56) References Cited

U.S. PATENT DOCUMENTS

| | | |
|---|---|---|
| 2,729,211 A | 1/1956 | Peter |
| 3,751,305 A | 8/1973 | Huebscher |
| 3,788,318 A | 1/1974 | Kim et al. |
| 3,828,770 A | 8/1974 | Kuris et al. |
| 3,828,782 A | 8/1974 | Polin |
| 4,000,739 A | 1/1977 | Stevens |
| 4,241,289 A | 12/1980 | Bowling |
| 4,445,892 A | 5/1984 | Hussein et al. |
| 4,590,669 A | 5/1986 | Imamura |
| 4,634,432 A | 1/1987 | Kocak |
| 4,637,814 A | 1/1987 | Leiboff |
| 4,650,466 A | 3/1987 | Luther |
| 4,650,472 A | 3/1987 | Bates |
| 4,682,981 A | 7/1987 | Suzuki et al. |
| 4,705,511 A | 11/1987 | Kocak |
| 4,706,671 A | 11/1987 | Weinrib |

(Continued)

FOREIGN PATENT DOCUMENTS

EP 0696447 2/1996

(Continued)

OTHER PUBLICATIONS

Heuser article in Journal of Endovascular Surgery 1995-1 pp. 81-88.

(Continued)

*Primary Examiner*—Suzette Gherbi
(74) *Attorney, Agent, or Firm*—Kolisch Hartwell, P.C.

(57) ABSTRACT

A stent is provided with a multi-layer structure, combining one or more mesh layers with one or more film layers. The film layer(s) are configured to substantially prevent growth of an inner lining of a blood vessel, where the stent is placed, through the mesh layer(s). The end-to-end length of the film layer(s) may be greater than the lengths of the mesh layer(s) by at least about 0.5 mm. The mesh and film layers include a radiopaque portion adjacent their ends to provide an X-ray indication of whether the mesh layer(s) have expanded beyond the ends of the film layer(s). If the stent includes inner and outer film layers and a middle mesh layer, the film layers may be sealed together adjacent the ends, encasing and fixing in place the middle layer. The mesh layer may be constructed to be more compliant adjacent its distal end and to expand more rapidly in response to expansion of a balloon catheter as compared to a middle portion of the mesh layer.

10 Claims, 10 Drawing Sheets

U.S. PATENT DOCUMENTS

| | | |
|---|---|---|
| 4,744,364 A | 5/1988 | Kensey |
| 4,771,777 A | 9/1988 | Horzewski et al. |
| 4,772,258 A | 9/1988 | Marangoni et al. |
| 4,796,640 A | 1/1989 | Webler |
| 4,832,688 A | 5/1989 | Sagae et al. |
| 4,862,891 A | 9/1989 | Smith |
| 4,874,378 A | 10/1989 | Hillstead |
| 4,883,460 A | 11/1989 | Zanetti |
| 4,895,564 A | 1/1990 | Farrell |
| 4,911,163 A | 3/1990 | Fina |
| 4,950,257 A | 8/1990 | Hibbs et al. |
| 4,994,071 A | 2/1991 | MacGregor |
| 5,092,846 A | 3/1992 | Nishijima et al. |
| 5,112,310 A | 5/1992 | Grobe |
| 5,147,336 A | 9/1992 | Wendell et al. |
| 5,163,906 A | 11/1992 | Ahmadi |
| 5,176,144 A | 1/1993 | Yoshikoshi et al. |
| 5,183,470 A | 2/1993 | Wettermann |
| 5,199,939 A | 4/1993 | Dake et al. |
| 5,207,228 A | 5/1993 | Roelandt et al. |
| 5,213,417 A | 5/1993 | Yamada et al. |
| 5,217,019 A | 6/1993 | Hughes |
| 5,217,484 A | 6/1993 | Marks |
| 5,234,437 A | 8/1993 | Sepetka |
| 5,242,410 A | 9/1993 | Melker |
| 5,256,141 A | 10/1993 | Gencheff et al. |
| 5,256,158 A | 10/1993 | Tolkoff et al. |
| 5,257,979 A | 11/1993 | Jagpal |
| 5,261,878 A | 11/1993 | Galindo |
| 5,267,966 A | 12/1993 | Paul |
| 5,275,488 A | 1/1994 | Stelts |
| 5,281,793 A | 1/1994 | Gavin et al. |
| 5,290,310 A | 3/1994 | Makower et al. |
| 5,292,311 A | 3/1994 | Cope |
| 5,320,617 A | 6/1994 | Leach |
| 5,330,486 A | 7/1994 | Wilk |
| 5,354,271 A | 10/1994 | Voda |
| 5,356,486 A | 10/1994 | Sugarman et al. |
| 5,364,392 A | 11/1994 | Warner et al. |
| 5,370,459 A | 12/1994 | Culbertson et al. |
| 5,380,304 A | 1/1995 | Parker |
| 5,395,341 A | 3/1995 | Slater |
| 5,403,341 A | 4/1995 | Solar |
| 5,415,635 A | 5/1995 | Bagaoisan et al. |
| 5,423,774 A | 6/1995 | Fischell et al. |
| 5,437,292 A | 8/1995 | Kipshidze et al. |
| 5,439,446 A | 8/1995 | Barry |
| 5,443,478 A | 8/1995 | Purdy |
| 5,445,646 A | 8/1995 | Euteneuer et al. |
| 5,458,573 A | 10/1995 | Summers |
| 5,462,359 A | 10/1995 | Reichl et al. |
| 5,462,529 A | 10/1995 | Simpson et al. |
| 5,466,230 A | 11/1995 | Davila |
| 5,499,975 A | 3/1996 | Cope et al. |
| 5,512,291 A | 4/1996 | Li |
| 5,514,236 A | 5/1996 | Avellanet et al. |
| 5,545,193 A | 8/1996 | Fleischman et al. |
| 5,545,209 A | 8/1996 | Roberts et al. |
| 5,549,626 A | 8/1996 | Miller et al. |
| 5,578,008 A | 11/1996 | Hara |
| 5,591,137 A | 1/1997 | Stevens |
| 5,591,206 A | 1/1997 | Moufarrege |
| 5,599,325 A | 2/1997 | Ju et al. |
| 5,620,457 A | 4/1997 | Pinchasik et al. |
| 5,628,786 A | 5/1997 | Banas et al. |
| 5,632,760 A | 5/1997 | Sheiban et al. |
| 5,632,762 A | 5/1997 | Myler |
| 5,645,560 A | 7/1997 | Crocker et al. |
| 5,660,473 A | 8/1997 | Noma et al. |
| 5,665,107 A | 9/1997 | Hammerslag |
| 5,667,523 A * | 9/1997 | Bynon et al. ............... 623/1.13 |
| 5,674,241 A | 10/1997 | Bley et al. |
| 5,681,295 A | 10/1997 | Gyure et al. |
| 5,683,453 A | 11/1997 | Palmaz |
| 5,688,266 A | 11/1997 | Edwards et al. |
| 5,695,498 A | 12/1997 | Tower |
| 5,707,359 A | 1/1998 | Bufalini |
| 5,725,524 A | 3/1998 | Mulier et al. |
| 5,725,572 A * | 3/1998 | Lam et al. ................. 623/1.16 |
| 5,728,068 A | 3/1998 | Leone et al. |
| 5,733,044 A | 3/1998 | Rose et al. |
| 5,735,892 A | 4/1998 | Myers et al. |
| 5,743,900 A | 4/1998 | Hara |
| 5,749,880 A | 5/1998 | Banas et al. |
| 5,769,077 A | 6/1998 | Lindegren |
| 5,792,070 A | 8/1998 | Kauphusman et al. |
| 5,800,393 A | 9/1998 | Sahota |
| 5,800,520 A | 9/1998 | Fogarty et al. |
| 5,807,350 A | 9/1998 | Diaz |
| 5,814,016 A | 9/1998 | Valley et al. |
| 5,814,064 A | 9/1998 | Daniel et al. |
| 5,820,607 A | 10/1998 | Tcholakian et al. |
| 5,830,222 A | 11/1998 | Makower |
| 5,830,224 A | 11/1998 | Cohn et al. |
| 5,833,644 A | 11/1998 | Zadno-Azizi et al. |
| 5,833,650 A | 11/1998 | Imran |
| 5,843,124 A | 12/1998 | Hammerslag |
| 5,843,166 A * | 12/1998 | Lentz et al. ............... 623/1.13 |
| 5,853,409 A | 12/1998 | Swanson et al. |
| 5,855,563 A | 1/1999 | Kaplan et al. |
| 5,857,998 A | 1/1999 | Barry |
| 5,868,708 A | 2/1999 | Hart et al. |
| 5,893,867 A | 4/1999 | Bagaoisan et al. |
| 5,897,497 A | 4/1999 | Fernandez |
| 5,899,917 A | 5/1999 | Edwards et al. |
| 5,906,636 A | 5/1999 | Casscells, III et al. |
| 5,911,710 A | 6/1999 | Barry et al. |
| 5,916,264 A * | 6/1999 | Von Oepen et al. ....... 623/1.15 |
| 5,928,260 A | 7/1999 | Chin et al. |
| 5,928,279 A | 7/1999 | Shannon et al. |
| 5,935,075 A | 8/1999 | Casscells et al. |
| 5,938,694 A | 8/1999 | Jaraczewski et al. |
| 5,944,019 A | 8/1999 | Knudson et al. |
| 5,957,961 A | 9/1999 | Maguire et al. |
| 5,964,798 A | 10/1999 | Imran |
| 5,968,064 A | 10/1999 | Selmon et al. |
| 5,976,178 A | 11/1999 | Goldsteen et al. |
| 5,980,532 A | 11/1999 | Wang |
| 5,984,955 A | 11/1999 | Wisselink |
| 5,989,223 A | 11/1999 | Chu et al. |
| 5,997,526 A | 12/1999 | Giba et al. |
| 6,004,310 A | 12/1999 | Bardsley et al. |
| 6,013,085 A | 1/2000 | Howard |
| 6,017,365 A | 1/2000 | Von Oepen |
| 6,019,779 A | 2/2000 | Thorud et al. |
| 6,022,336 A | 2/2000 | Zadno-Azizi et al. |
| 6,022,343 A | 2/2000 | Johnson et al. |
| 6,030,406 A | 2/2000 | Davis et al. |
| 6,033,434 A | 3/2000 | Borghi |
| 6,064,902 A | 5/2000 | Haissaguerre et al. |
| 6,068,656 A | 5/2000 | Von Oepen |
| 6,071,292 A | 6/2000 | Makower et al. |
| 6,120,534 A * | 9/2000 | Ruiz ........................ 623/1.19 |
| 6,124,523 A | 9/2000 | Banas et al. |
| 6,156,064 A | 12/2000 | Chouinard |
| 6,159,197 A | 12/2000 | Heuser |
| 6,168,579 B1 | 1/2001 | Tsugita |
| 6,176,872 B1 | 1/2001 | Miksza |
| 6,187,033 B1 | 2/2001 | Schmitt et al. |
| 6,190,353 B1 | 2/2001 | Makower et al. |
| 6,193,747 B1 | 2/2001 | von Oepen |
| 6,245,052 B1 | 6/2001 | Orth et al. |
| 6,264,685 B1 | 7/2001 | Ahari |
| 6,264,690 B1 | 7/2001 | Von Oepen |

| | | | |
|---|---|---|---|
| 6,283,958 B1 | 9/2001 | Vogl et al. | |
| 6,308,090 B1 | 10/2001 | Tu et al. | |
| 6,325,826 B1 | 12/2001 | Vardi et al. | |
| 6,364,900 B1 | 4/2002 | Heuser | |
| 6,383,214 B1* | 5/2002 | Banas et al. | 623/1.14 |
| 6,408,214 B1 | 6/2002 | Williams et al. | |
| 6,464,665 B1 | 10/2002 | Heuser | |
| 6,464,684 B1 | 10/2002 | Galdonik | |
| 6,530,914 B1 | 3/2003 | Mickley | |
| 6,536,949 B1 | 3/2003 | Heuser | |
| 6,582,394 B1 | 6/2003 | Reiss et al. | |
| 6,613,078 B1* | 9/2003 | Barone | 623/1.13 |
| 6,638,268 B2 | 10/2003 | Niazi | |
| 6,673,102 B1* | 1/2004 | Vonesh et al. | 623/1.13 |
| 6,709,455 B1* | 3/2004 | Chouinard | 623/1.32 |
| 6,746,479 B2 | 6/2004 | Ehr et al. | |
| 6,830,568 B1 | 12/2004 | Kesten et al. | |
| 6,858,038 B2 | 2/2005 | Heuser | |
| 6,866,805 B2* | 3/2005 | Hong et al. | 264/161 |
| 7,166,088 B2 | 1/2007 | Heuser | |
| 7,179,250 B2 | 2/2007 | Heuser | |
| 2001/0003161 A1 | 6/2001 | Vardi et al. | |
| 2002/0178570 A1* | 12/2002 | Sogard et al. | 29/516 |
| 2003/0055402 A1 | 3/2003 | Zhou | |
| 2003/0055484 A1* | 3/2003 | Lau et al. | 623/1.13 |
| 2003/0139797 A1* | 7/2003 | Johnson et al. | 623/1.13 |
| 2003/0199967 A1* | 10/2003 | Hartley et al. | 623/1.13 |
| 2004/0019373 A1* | 1/2004 | Casey et al. | 623/1.13 |
| 2004/0082989 A1* | 4/2004 | Cook et al. | 623/1.13 |
| 2004/0098095 A1* | 5/2004 | Burnside et al. | 623/1.13 |
| 2004/0106978 A1* | 6/2004 | Greenberg et al. | 623/1.13 |
| 2004/0162603 A1* | 8/2004 | Golds et al. | 623/1.13 |
| 2004/0167607 A1* | 8/2004 | Frantzen | 623/1.13 |
| 2005/0125011 A1 | 6/2005 | Spence et al. | |
| 2006/0047222 A1 | 3/2006 | Heuser | |
| 2006/0217799 A1 | 9/2006 | Mailander et al. | |
| 2007/0038290 A1* | 2/2007 | Huang et al. | 623/1.16 |
| 2007/0043423 A1* | 2/2007 | Grewe | 623/1.11 |
| 2007/0073383 A1* | 3/2007 | Yip et al. | 623/1.16 |

FOREIGN PATENT DOCUMENTS

| | | |
|---|---|---|
| EP | 0707864 | 4/1996 |
| EP | 0917886 | 5/1999 |
| EP | 1421970 | 5/2004 |
| FR | 2753907 | 3/1998 |
| JP | 0003094773 | 4/1991 |
| WO | WO9640348 | 12/1996 |
| WO | WO9717101 | 5/1997 |
| WO | WO98/00090 | 1/1998 |
| WO | WO9811933 | 3/1998 |
| WO | WO98/19632 | 5/1998 |
| WO | WO98/26731 | 6/1998 |
| WO | WO98/39047 | 9/1998 |
| WO | WO99/08744 | 2/1999 |
| WO | WO9913808 | 3/1999 |
| WO | WO99/24105 | 5/1999 |
| WO | WO9934749 | 7/1999 |
| WO | WO9936002 | 7/1999 |
| WO | WO0166038 | 3/2001 |
| WO | WO0596995 | 10/2005 |

OTHER PUBLICATIONS

English Abstract of JP0003094773 of Inaba et al.
English Abstract of FR2753907 of Boussignac et al., from WO/98/14233 publication, from which FR2753907 claims priority.

Baffour, M.S.C., R. et al. "An Angiographic Study of Ischemia as a Determinant of Neovascularization in Arteriovenous Reversal." Surgery, Gynecology & Obstetrics. Jan. 1988. pp. 28-32. vol. 166.

Bernheim, M.D., "Arteriovenous Anastomosis-Reversal of the Circulation-As a Preventative of Gangrene of the Extremeties." Arteriovenous Anastomosis. Undated.

Blaisdell, M.D., William, et al., "Revascularization of Severly Ischemic Extremeties with an Arteriovenous Fistula." American Journal of Surgery. Aug. 1966. pp. 166-174. vol. 112.

Cuttino Jr., John, et al. "Collateral Vessel Formation: Isolation of a Transferrable Factor Promoting a Vascular Response." Basic Research in Cardiology. Jan. 9, 1975. pp. 568-573. vol. 70, No. 5.

Gerard, M.D., Dava, et al. "Acute Physiologic Effects of Arteriovenous Anastomosis and Fistula in Revascularizing the Ischemic Canine Hind Limb." Surgery. Apr. 1981. pp. 485-493. vol. 89, No. 4.

Goldsmith, M.D., Harry, et al. "Lipid Angiogenic Factor from Omentum." JAMA. Oct. 19, 1984. pp. 2034-2036. vol. 252, No. 15.

Halstead, M.D., Albert. "Arteriovenous Anastomosis in the Treatment of Gangrene in the Extremities." Surgery, Gynecology and Obstetrics. 1912. pp. 1-19. vol. 16.

Howell, M.D., Marcus, et al. "Preliminary Results of Endovascular Abdominal Aortic Aneurysm Exclusion with the AneuRx Stent-Graft." Journal of the American College of Cardiology. 2001. pp. 1040-1048. vol. 38, No. 4.

Johnson & Johnson Gateway, LLC. "Chronic Total Occlusion (CTO) Technologies." http://www.jnjgateway.com/home.jhtml?loc=USENG&page=viewContent&contentId=09008b9881163810&parentId=09908b9881163810.2007. Printed Jan. 17, 2007.

Kalmar, M.D., Gabor, et al. "Radial Force and Wall Apposition of Balloon-expamdable Vascular Stents in Eccentric Stenoses: An In Vitro Evaluation in a Curved Vessel Model." Journal of Vascular and Interventional Radiology. May 2002. pp. 499-508. vol. 13, No. 5.

Kumar, S., et al. "Angiogenesis Factor from Human Myocardial Infarcts." The Lancet. Aug. 13, 1983. pp. 364-368.

Matolo, M.D., Nathaniel. "Use of an Arteriovenous Fistula for Treatment of the Severly Ischemic Extremity: Experimental Evaluation." Ann. Surg. Nov. 1976. pp. 622-625. vol. 184, No. 5.

Oesterle, et al. "An Embolization Containment Device." Catheterization and Cardiovascular Interventions. 1999. pp. 243-250. vol. 47.

Robertson, M.D., Roy et al. "Collateral Circulation in the Presence of Experimental Arteriovenous Fistula." Surgery. Jan. 1950. pp. 1-16. vol. 27, No. 1.

Root, M.D., Harlan, et al. "Effects of an Arteriovenous Fistula on the Devascularized Limb." JAMA. Feb. 22, 1965. pp. 109-112. vol. 191, No. 8.

Rossi, Anne V. "510(k) Summary per 21 CFR 807.92 re BSC IQ Hydrophilic Guide Wire and Response Letter from Department of Health and Human Services." Aug. 1, 2003.

Sheil, A.G.R. "Treatment of Critical Ischaemia of the Lower Limb by Venous Arterialization: an Interim Report." Br. J. Surg. 1977. pp. 197-199.

Szilagyi, M.D., Emerick. "Femoral Arteriovenous Anastomosis in the Treatment of Occlusive Arterial Disease." A.M.A. Archives of Surgery. Undated.

Terumo Medical Corporation. "Glidewire Hydrophilic Coated Guidewire Designed for Peripheral Applications." http://www.terumomedical.com/SubDepts.asp?myID=79. Printed Jan. 30, 2007.

* cited by examiner

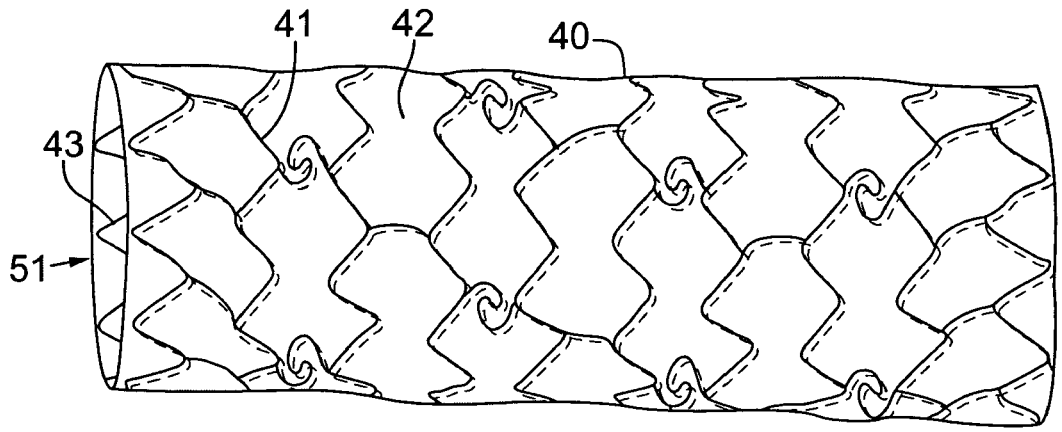
FIG. 1a Expanded Stent
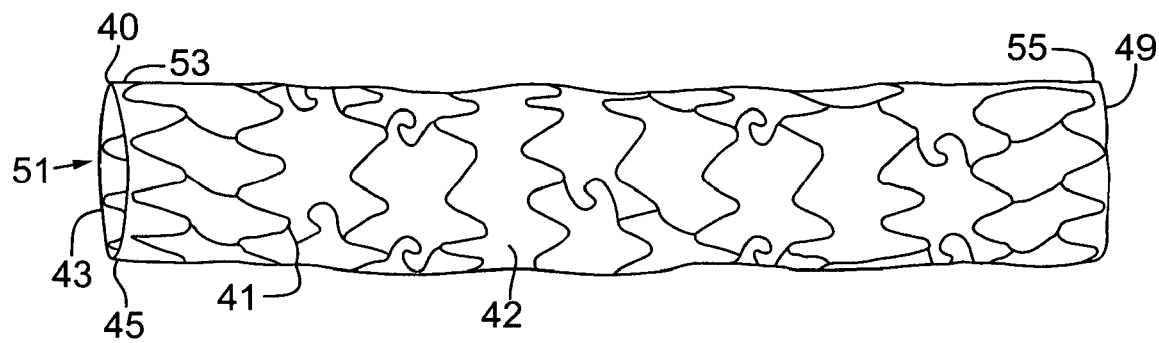
FIG. 1b
Compressed or Pre-expanded Stent

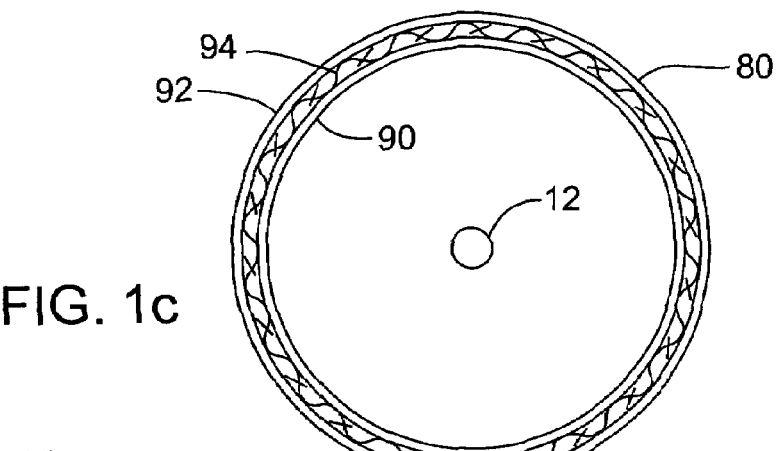
FIG. 1c
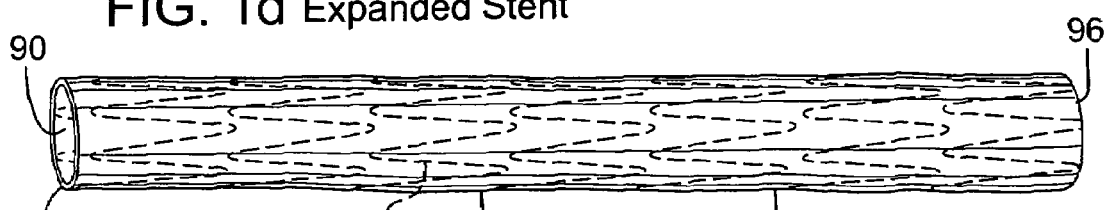
FIG. 1d Expanded Stent
FIG. 1e Compressed or Pre-expanded Stent
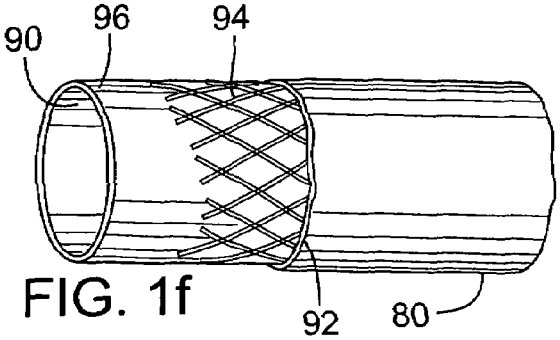
FIG. 1f

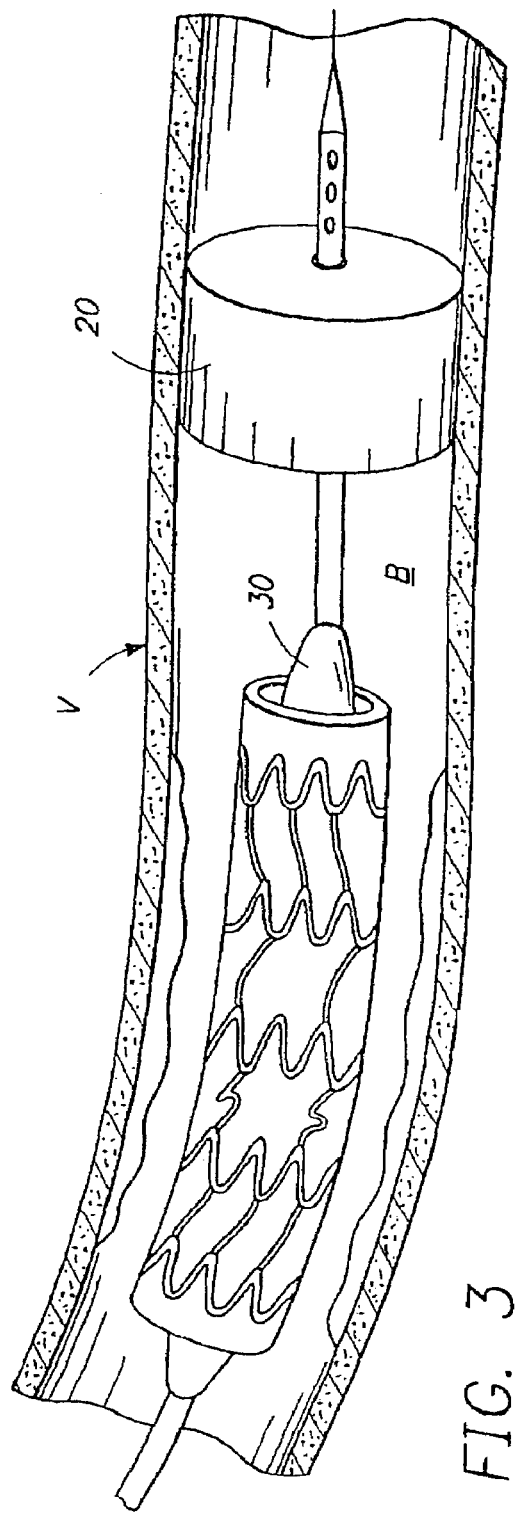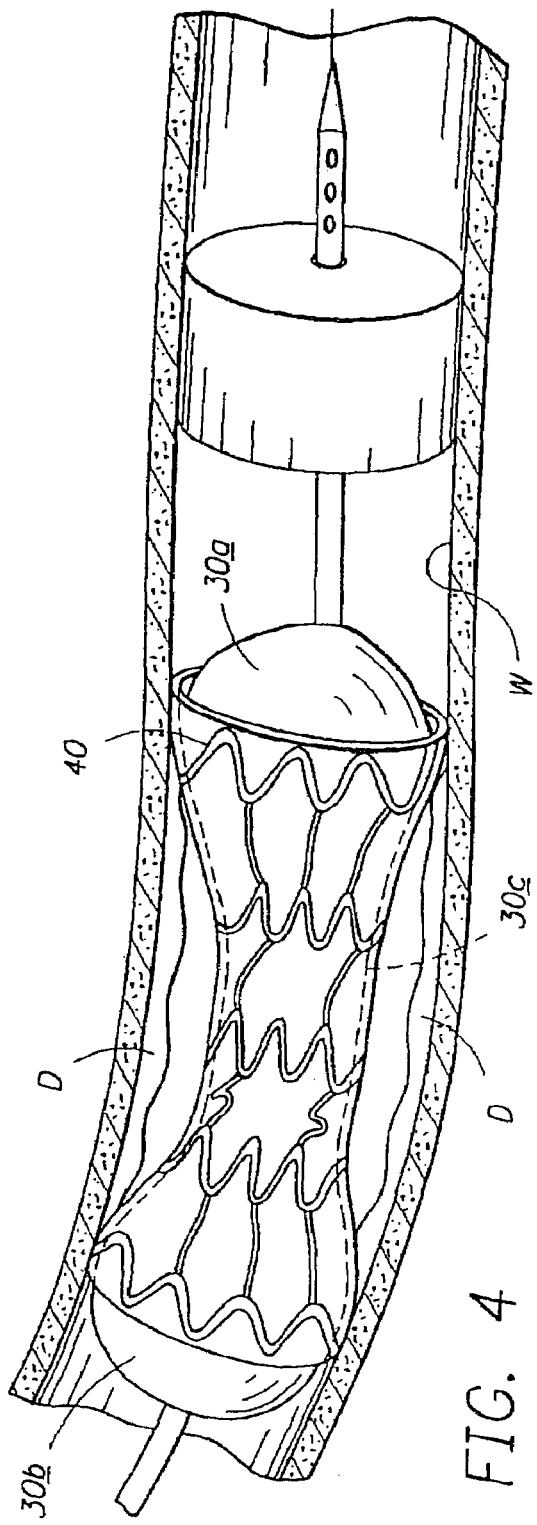

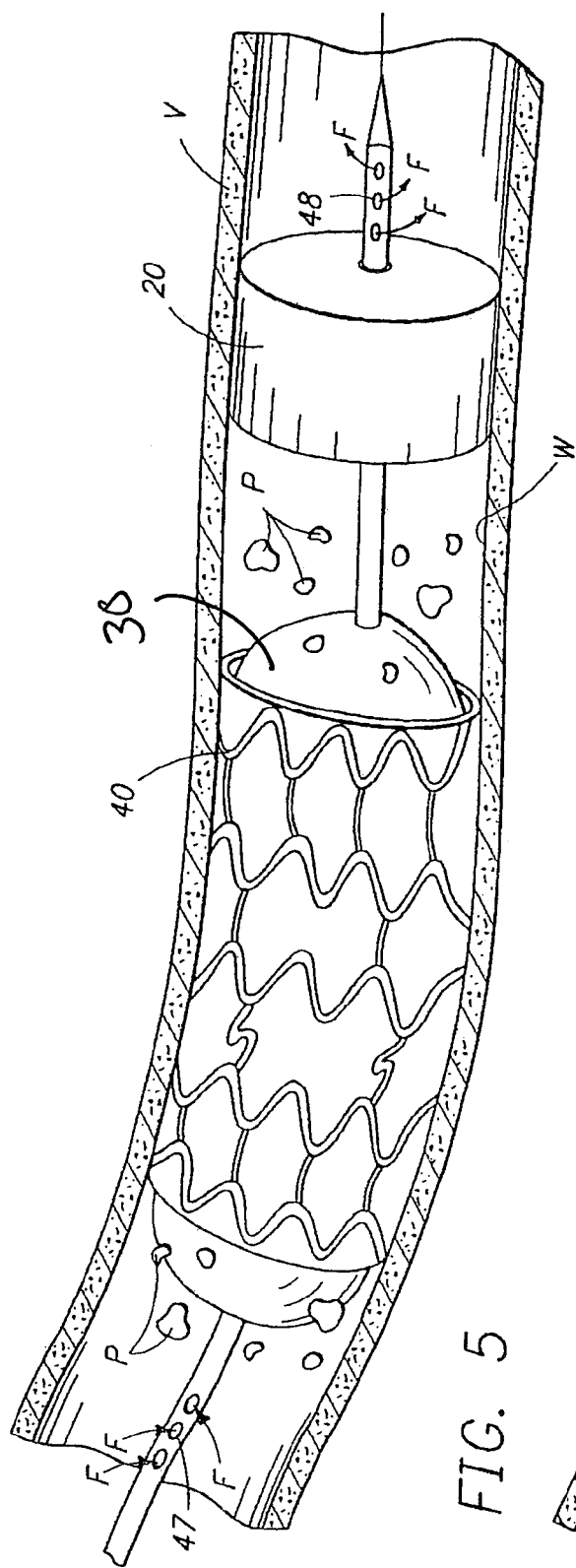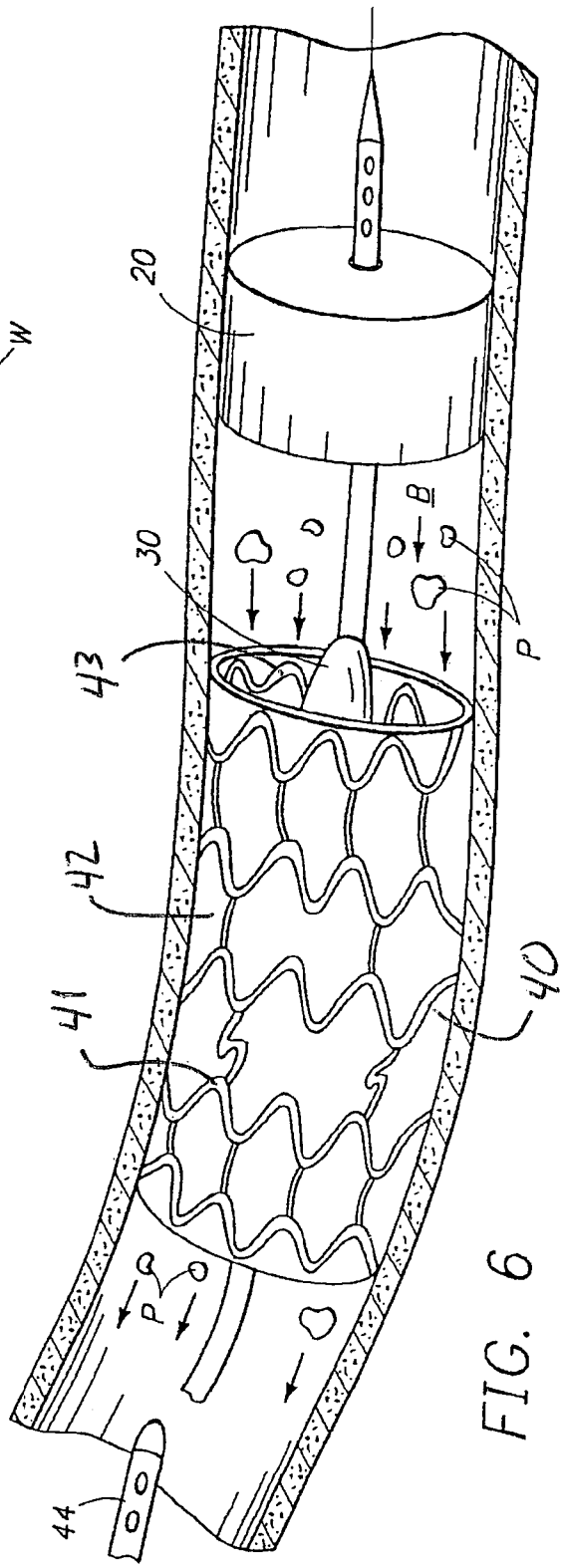
FIG. 5
FIG. 6

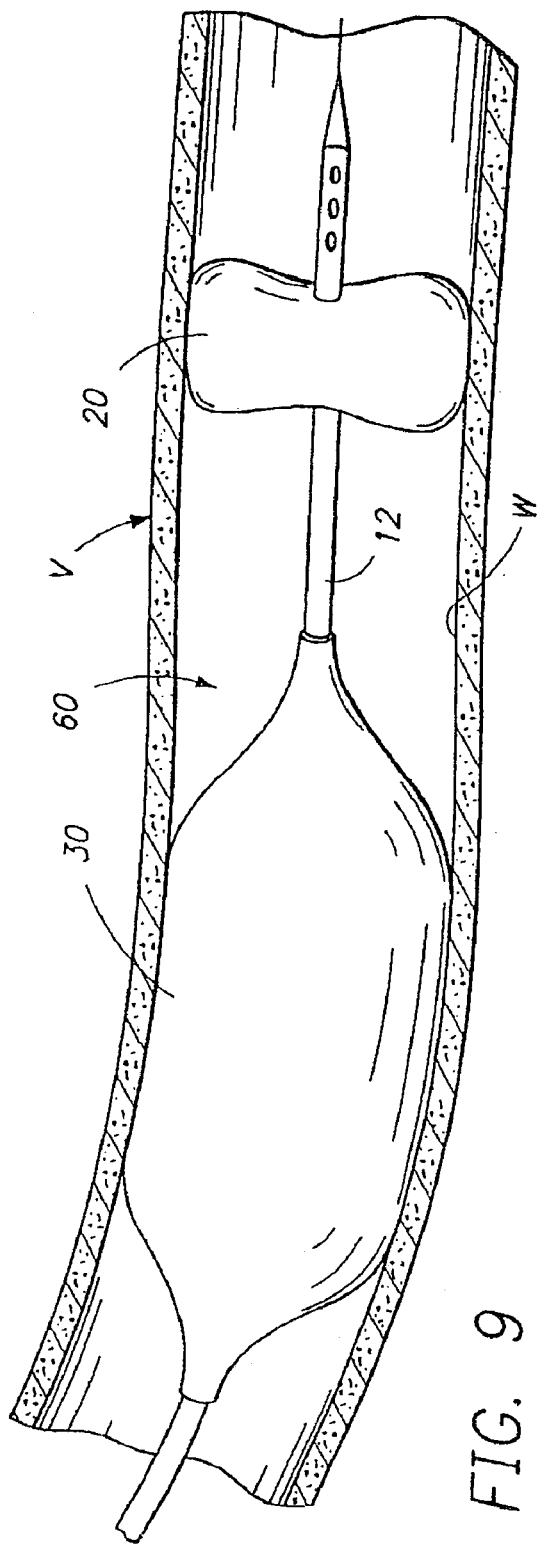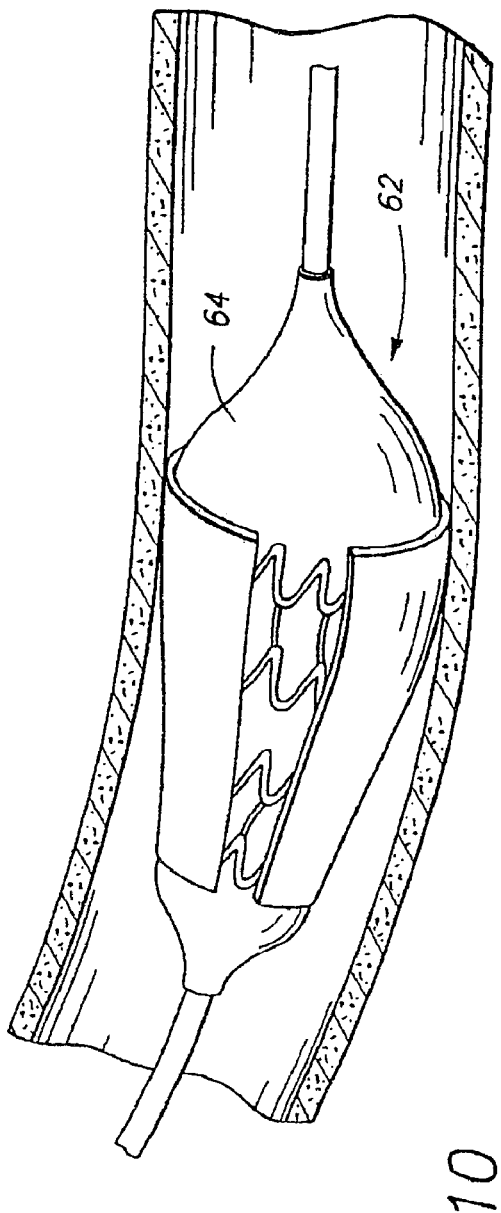
FIG. 9
FIG. 10

Distal Portion of
Stent is Thinner
Metal

Stent Dilation
Showing the
Thinner Area
Dialating First

From Bottom to
Top Gradually
Thicker Metal

Balloon Inflating with
Distal End Opening First

Further Inflation of Balloon
Showing Complete Inflation

Balloon Inflating with
Distal End Opening First

Proximal End Inflating Second

Full Balloon Inflation

STENT WITH COVERING AND DIFFERENTIAL DILATION

CROSS REFERENCE TO RELATED APPLICATION

This application is related to U.S. Provisional Patent Application No. 60/419,508, filed on Oct. 17, 2002 for a STENT WITH COVERING AND DIFFERENTIAL DILATION, the disclosure of which is hereby incorporated by reference.

BACKGROUND

A physician places a stent into a human blood vessel in response to several different types of conditions, including a weakening or rupture of the blood vessel or a narrowing of the vessel. The stent is intended to maintain a leak-free channel through the vessel for blood flow. The stent is made of biocompatible materials because it is in direct contact with an inner lining, or intima, of the blood vessel and with the blood. A stent made of wire mesh, when inserted into the blood vessel, tends to allow growth of the intima between and through the mesh. Such growth, or neointimal proliferation, can constrict or close the channel that the stent is intended to provide. Stents with two layers of mesh and a PTFE layer in between have been used, but these have all included a portion of the wire mesh extending beyond the ends of the PTFE layer, providing an area for neointimal proliferation.

The stents with two layers of mesh with a PTFE layer in between have a disadvantage produced by the outer mesh layer's directly contacting the intima. The direct exposure of the intima to the metal of the mesh layer may promote embolic events and restenosis. Expansion of the stent into place in the blood vessel, in particular at an area of stenosis caused by plaque, can disturb and break away small pieces of plaque or emboli, raising the risk of embolism if the emboli are allowed to travel downstream in the blood.

SUMMARY OF THE INVENTION

An embodiment of the present invention provides a stent with generally cylindrical inner and outer mesh layers, and a generally cylindrical film layer fitted between the inner and outer layers with the ends of the film layer extending beyond the ends of the inner and outer layers.

Another embodiment of the present invention provides a stent formed with an inner film layer and an outer film layer that provide flexible coverings, and a middle wire mesh layer. The inner and outer layers may be sized to the same length and both may be longer than the length of the middle layer. The adjoining ends of the inner and outer layers may be sealed together, encasing the middle layer.

For either of the foregoing embodiments for the stent, radiopaque portions may be provided adjacent the ends of the inner, outer, and middle layers to allow for an X-ray-viewable indication of the stent expanded in place in a blood vessel to determine whether the mesh layer or layers have expanded beyond the ends of the film layer or layers.

Another embodiment of the present invention provides a stent delivery system including a stent with a mesh layer having a middle portion between open, opposed proximal and distal ends and a central lumen communicating between the open ends. The mesh layer includes a wire structure, and the stent delivery system further includes a balloon catheter for mounting the stent and inserting and installing the stent inside the human blood vessel. The wire structure of the mesh layer adjacent the distal end is constructed to be more compliant and to expand more rapidly in response to expansion of the balloon catheter as compared to the middle portion and proximal end of the mesh layer.

BRIEF DESCRIPTION OF THE DRAWINGS

FIG. 1a is an isometric view of a stent for use in the present invention, the stent in an expanded or dilated condition.

FIG. 1b is an isometric view of the stent of FIG. 1a for use in the present invention, the stent in a pre-expanded or compressed condition.

FIG. 1c is a cross-sectional view of an alternative embodiment for a stent of the present invention, showing the layers of the stent.

FIG. 1d is an isometric view of the stent of FIG. 1c, the stent in an expanded or dilated condition.

FIG. 1e is an isometric view of the stent of FIG. 1c, the stent in a pre-expanded or compressed condition.

FIG. 1f is a partially cutaway, isometric view of the stent of FIG. 1c.

FIG. 3 is a side elevational view of the stent delivery system of FIG. 1, showing a step in the stent delivery.

FIG. 4 is a side elevational view of the stent delivery system of FIG. 1, showing a second step in the stent delivery.

FIG. 5 is a side elevational view of the stent delivery system of FIG. 1, showing a third step in the stent delivery.

FIG. 6 is a side elevational view of the stent delivery system of FIG. 1, showing a fourth step in the stent delivery.

FIG. 9 is a side elevational view of a predication system according to another embodiment of the invention.

FIG. 10 is a side elevational view of a stent delivery system according to another embodiment of the invention.

DETAILED DESCRIPTION OF THE DRAWINGS AND BEST MODE FOR CARRYING OUT THE INVENTION

Figure 1:
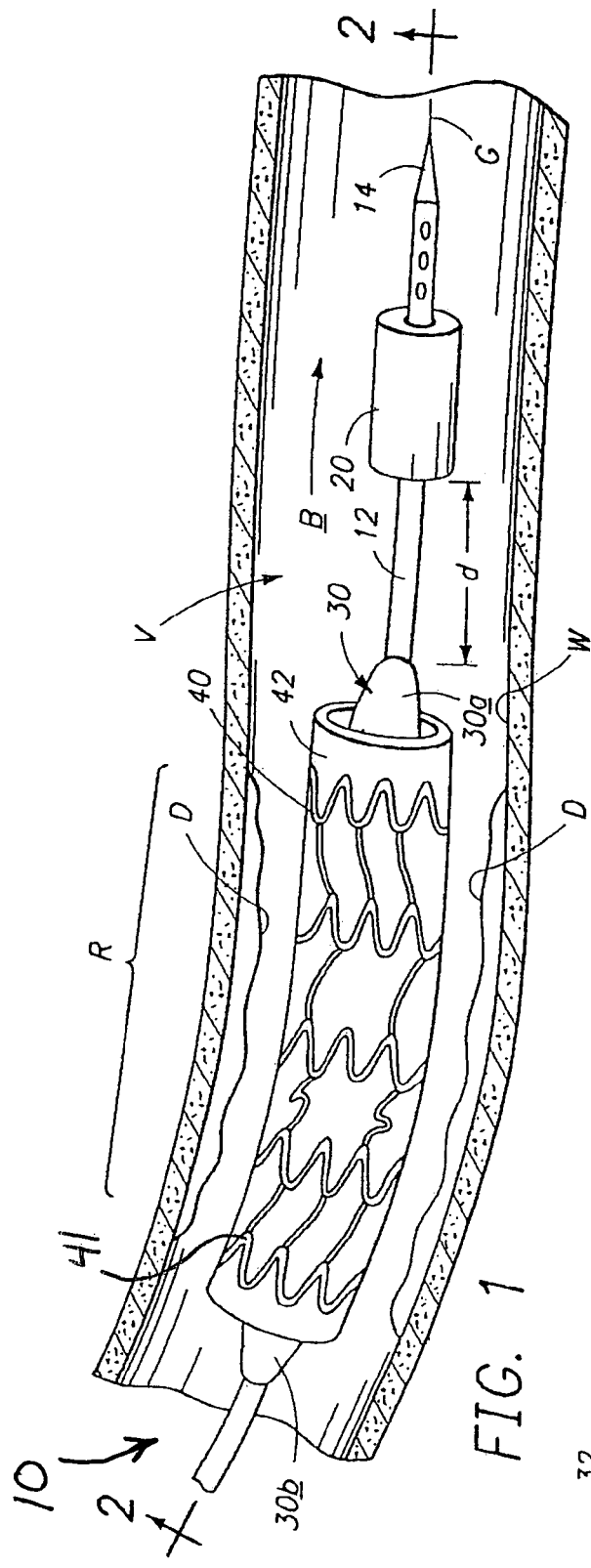
FIG. 1 is a side elevational view of a stent delivery system according to an embodiment of the invention.
Figure 2:
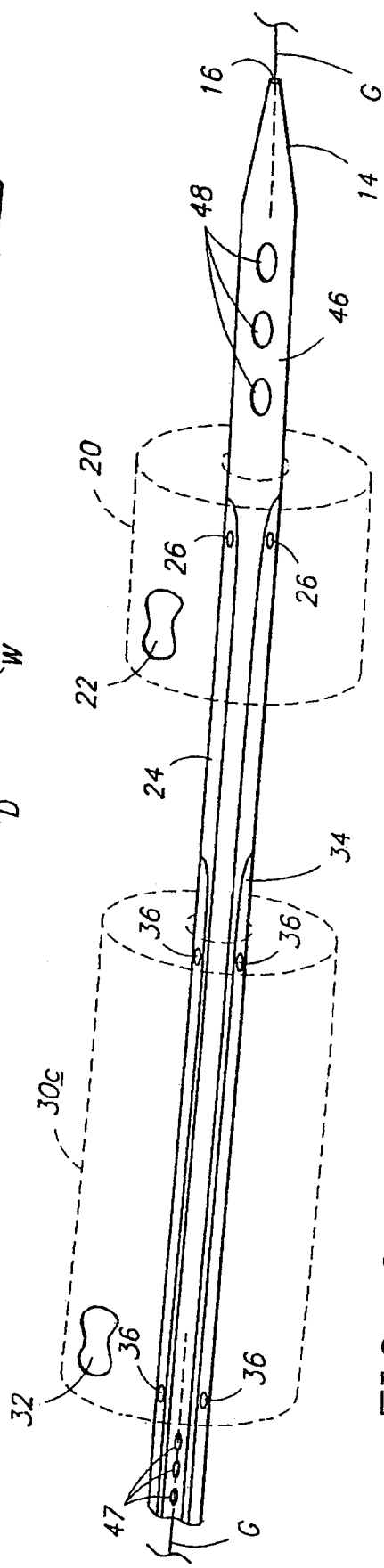
FIG. 2 is a sectional view of the catheter shown in FIG. 1, the sectional view being taken along lines 2-2 of FIG. 1.

An embodiment of the invention is depicted in FIGS. 1 and 2, in which a stent delivery system is indicated generally by reference number 10. System 10 includes a transporting mechanism, such as catheter 12, that is movable within a vessel V. The vessel may be a vein, artery, tracheal channel, or may form part of the urinary, renal, or other fluid-transporting systems within a body. However, the embodiment shown in the figures relates specifically to a vein or artery having blood B flowing therethrough. Catheter 12 has a tapered distal end 14. A guide wire aperture 16 is provided at distal end 14 to permit the catheter to be threaded upon a guide wire G as is known in the art. For clarity, guide wire G is not shown in the interior of catheter 12 in FIG. 2.

A conduit blocking mechanism, shown in the figures as a first flexible membrane 20, is disposed upon catheter 12 adjacent proximal distal end 14. First flexible membrane 20 encloses a first space 22 that increases and decreases in volume as the first flexible membrane is inflated and deflated. In a preferred embodiment, first flexible membrane 20 is a very compliant, non-tissue-traumatic balloon that expands to a diameter of about 3-10 mm when fully inflated. A first lumen or channel 24 is provided within catheter 12 that communicates, through first apertures 26, with first space 22. A first controlling fluid, such as a saline mixed with I.V. contrast, passes through first channel 24, through first apertures 26, and into first space 28 to inflate and deflate the first flexible membrane.

An instrument, such as second flexible membrane 30, is attached to catheter 12 at a distance d from first flexible membrane 20. Second flexible membrane 30 encloses a second space 32 that increases and decreases in volume as the first flexible membrane is inflated and deflated. Second flexible membrane 30 may comprise a very compliant, non-tissue-traumatic balloon that expands to a diameter of about 3-10 mm when fully inflated. A second lumen or channel 34 is provided within catheter 12 that communicates, through second apertures 36, with second space 32. A second controlling fluid, such as a saline with contrast, passes through second channel 34, through second apertures 36, and into second space 32 to inflate the second flexible membrane.

Second flexible membrane 30 has first and second ends 30a, 30b and an intermediate portion 30c disposed between the first and second ends.

A stent 40 is mounted in a compressed state upon second flexible membrane 30. As depicted in FIG. 1, stent 40 includes a non-self-expanding wire mesh structure, having a generally cylindrical shape that is configured to contact an interior lining or wall W of vessel V when expanded. Stent 40 includes a film layer such as covering 42 made of a flexible material such as polytetrafluoroethylene (PTFE). Stent 40 includes an outer mesh layer 41, and an inner mesh layer 43 (FIGS. 1a, 1b, and 5), with both layers preferably formed of metal wire, such as nitinol. As will be further described, other types of stents may also be used with the invention.

Film layer 42 preferably has a nominal shape that is generally cylindrical, including first and second opposed ends 45, 49 communicating with an interconnecting central lumen 51. Outer mesh layer 41 and inner mesh layer 43 likewise preferably have a nominal, pre-expanded or compressed shape that is generally cylindrical with first and second opposed ends 53, 55 communicating with an interconnecting central lumen, typically coaxial with that of the film layer 42. Each of the mesh and film layers define an end-to-end length, and preferably the end-to-end length of mesh layer 41 is greater than that of the mesh layers, which preferably are generally equal to one another. Preferably the film layer is about 0.5 mm longer than the mesh layers.

As best seen in FIGS. 1a, 1b, and 5, the inner mesh layer 43 is fitted within outer mesh layer 41 and the inner mesh layer thus has a nominal outer diameter less than an inner diameter of the outer mesh layer. The film layer is sized to fit between the outer mesh layer and the inner mesh layer.

An alternative embodiment of the stent of the present invention, which can be used in place of the stent just described, is shown in FIGS. 1c, 1d, 1e, and 1f. A stent 80 includes a wire mesh layer 94 encased within an inner flexible covering or film layer 90 and an outer flexible covering or film layer 92. The inner and outer layers are typically of substantially the same length and can be connected or sealed together, particularly adjacent ends 96. Mesh layer 94 is typically shorter in length than the inner and outer layers, preferably by about 0.5 mm, although, particularly in the case where the ends are sealed, the mesh layer may be substantially the same length as the inner and outer layers.

The inner and/or outer layers of stent 80 may be provided with a radiopaque portion adjacent first and second ends 96. A radiopaque portion of the middle layer, combined with the radiopaque portion of the inner and/or outer layer, allows for an X-ray examination of whether the middle layer has expanded beyond the ends of the inner and outer layers. That is, after stent 80 has been installed and expanded in a human blood vessel, the stent may be observed under an X-ray and the relative locations of the ends of the mesh layer and inner and outer layers may be determined. If either end of the mesh layer has extended beyond the ends of the inner and outer layers, the operator may consider retrieval of the stent or follow-up observation for any restenosis where the mesh layer has so extended. Stent 40 may similarly be provided with radiopaque portions adjacent the ends of its layers for a corresponding check of relative location of the ends when expanded in place in the blood vessel.

FIGS. 1 and 3-7 depict a method of using system 10 to insert stent 40 upon interior wall W. Guide wire G is inserted into vessel V according to known methods. A user directs catheter 12 into the vessel by sliding the catheter upon guide wire G so that stent 40 is positioned within a desired region R of the vessel, as depicted in FIG. 1. With respect to this embodiment, desired region R corresponds to a portion of the vessel having deposits D attached to interior wall W. Deposits D may be made of fatty or calcified material, or may comprise other material that at least partially obstructs the flow of blood B through the vessel. As shown in FIG. 3, the user inflates first flexible membrane 20. When fully inflated, first flexible membrane 20 substantially completely dams or blocks vessel V so that blood B cannot flow through the vessel. The user then inflates second flexible membrane 30. As shown in FIG. 4, second flexible membrane 30 may be designed so that first and second ends 30a and 30b are fully inflated prior to intermediate portion 30c being fully inflated. This inflating strategy is useful to entrap deposits D against the expanding stent, and prevents the deposits from being pushed or "kneaded" out from under the second flexible membrane. As second flexible membrane 30 expands during inflation, stent 40 also expands from its compressed state until it rests against interior wall W and deposits D to trap the deposits between the stent and the interior wall. When the second flexible membrane is fully inflated as shown in FIG. 5, stent 40 has undergone plastic deformation so that it is fully and permanently expanded against interior wall W. Second flexible membrane 30 is then deflated (FIG. 6), and stent 40 remains in contact with the interior wall.

Figure 7:
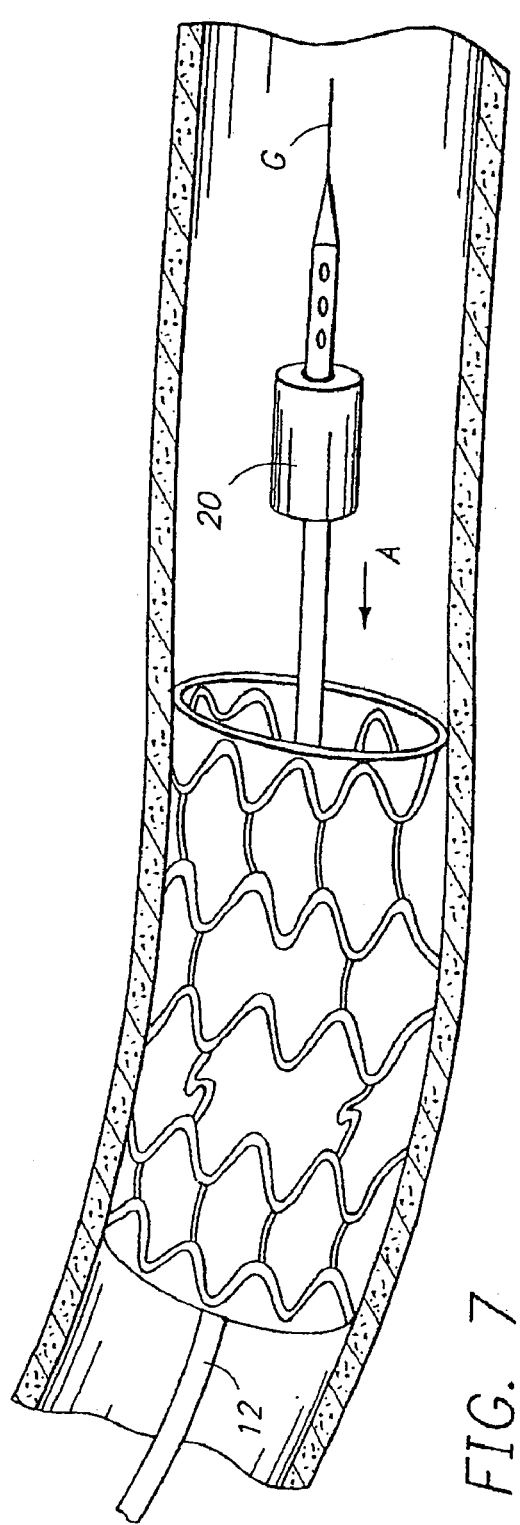
FIG. 7 is a side elevational view of the stent delivery system of FIG. 1, showing a fifth step in the stent delivery.

During the above process, portions of the deposits, which are shown as emboli P, may become dislodged from interior wall W. Emboli P may be of a size to cause an embolism if allowed to freely flow in the blood stream. The particles are removed by inserting a syringe 44 along a guiding catheter (not shown) into the vessel proximal second flexible membrane 30 and drawing blood B and emboli P into the syringe using known suction principles (FIG. 6). Syringe 44 may be a standard luer-lock syringe having a minimum capacity of 30 cc. First flexible membrane 20 is then deflated, as depicted in FIG. 7, to permit normal blood flow through the vessel. Catheter 12 is moved along guide wire G in the direction of arrow A to remove the catheter from the vessel. The guide wire is then removed according to known methods.

The steps in the stent installation method described above may be quickly and efficiently performed so that no embolism-forming particles are left in the blood after the first flexible membrane is deflated. The speed at which the method is performed reduces the time that blood flow is blocked. This in turn reduces the occurrence of ischemia and the resulting tissue damage due to lack of blood flow. Ischemic conditions may be further reduced by incorporating a perfusion apparatus within the catheter, which is depicted as a portion of system 10 in FIGS. 1 and 2. The perfusion apparatus includes a third lumen or channel 46 within the catheter. At least one perfusion inlet aperture 47 is disposed in catheter 12 proximal second end 30b of second flexible membrane. At least one perfusion outlet aperture 48 is disposed at distal end 14 of the catheter. Perfusion fluid F such as blood or other fluid flows into perfusion inlet apertures 47, through third channel 46, through perfusion outlet apertures 48 and into vessel V such that the perfusion fluid bypasses the inflated first and second flexible membranes 20, 30 (FIG. 5). In this manner, blood that has no embolism-forming particles contained therein flows through vessel V without interfering with the stent installation process. Perfusion inlet apertures may include one-way valves or check valves (not shown) to permit the flow of perfusion fluid only from perfusion inlet aperture 47 to perfusion outlet apertures 48. The valves close to prevent perfusion fluid from flowing out of perfusion inlet apertures 47 when syringe 44 is removing emboli from vessel V.

As described above, stent 40 is a non-self-expanding covered stent. A covered stent has been found to decrease restenosis, which is the regrowth of deposits D in region R after the stent has been installed therein. However, in certain circumstances it may be desirable to use an uncovered stent (not shown), which differs from stent 40 in that no covering 42 is provided.

Figure 8:
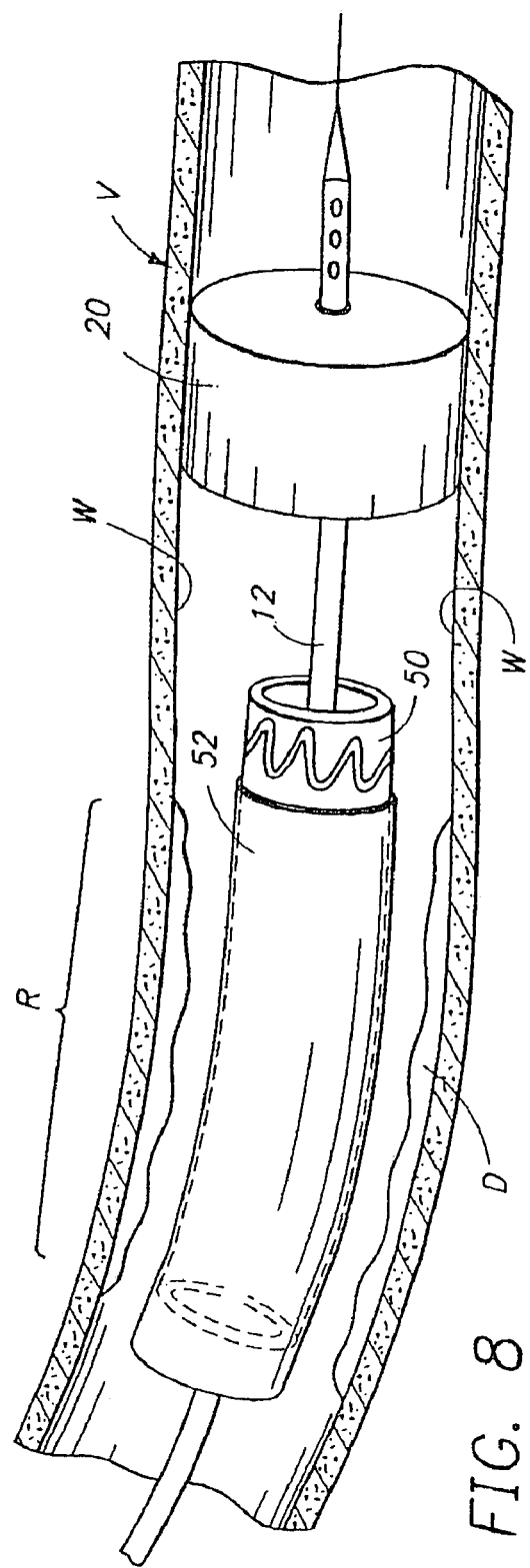
FIG. 8 is a side elevational view of a self-expanding stent delivery system according to the invention.

FIG. 8 depicts another type of stent, known as a self-expanding stent 50, which is usable with system 10. The self-expanding stent is a wire mesh cylinder that is constructed so that in a compressed state the stent is biased to expand to an expanded state. Such a stent does not require the use of a flexible membrane, such as second flexible membrane 30, to expand the stent. A sheath or sleeve 52 surrounds stent 50 while the stent is moved into region R by catheter 12. Once first flexible membrane 20 is inflated, sleeve 52 is removed from around stent 50 using known methods. Stent 50 expands to contact interior wall W of the vessel. Embolism-forming particles are then removed and the first flexible membrane is deflated as described above. Sleeve 52 and catheter 12 are then removed from vessel V using known methods.

The invention has been thus far described as being used to install a stent in a vessel. However, the invention is also useful for dilation or predication, which is the dilation of a vessel prior to performing a surgical or therapeutic technique or operation upon the vessel. FIG. 9 shows a system 60 according to the invention that may be used for predication. System 60 is similar in construction to system 10 depicted in FIG. 1, and similar components will therefore be identified by similar reference numbers. System 60 includes a catheter 12 and a first flexible membrane 20. A second flexible membrane 30 is attached to catheter 12. In this embodiment, second flexible membrane 30 is configured to be inflated until it contacts interior wall W and dilates vessel V. As with previous embodiments, first and second flexible membranes 20 and 30 are inflatable and deflatable independent of each other. System 60 is used in a manner similar to system 10 of FIGS. 1 and 3-7. Catheter 12 is inserted into vessel V and first flexible membrane 20 is inflated so that fluid flow through the vessel is substantially blocked. Second flexible membrane 30 is inflated to dilate the vessel. When sufficient dilation has been accomplished, the second flexible membrane is deflated and embolism-forming particles are evacuated using a syringe (not shown). First flexible membrane 20 is then deflated, and catheter 12 is removed from vessel V.

Figure 11:
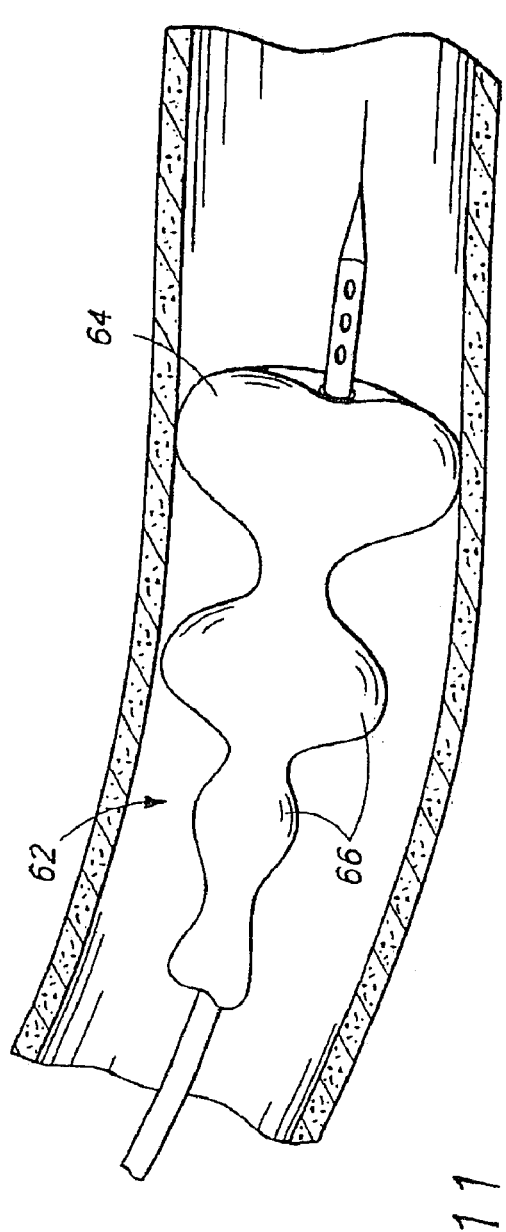
FIG. 11 is a side elevational view of a flexible membrane that may be used with a stent delivery system.
Figure 12:
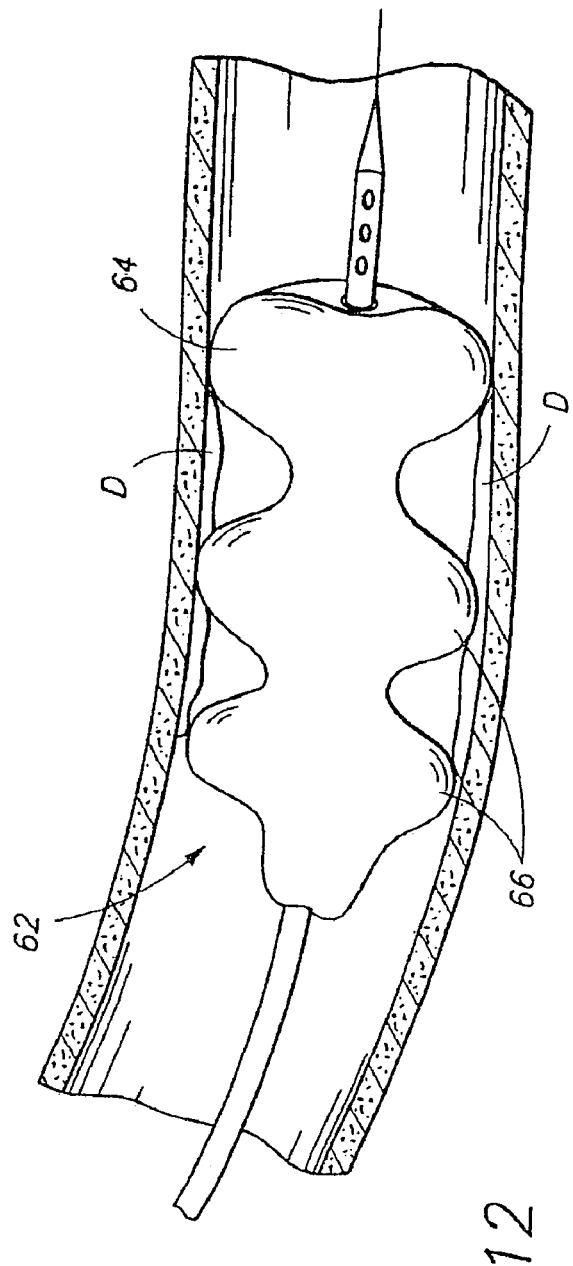
FIG. 12 is a side elevational view of another flexible membrane that may be used with a stent delivery system.

As previously discussed, second flexible membrane 30 is configured so that first and second ends 30a, 30b are fully inflated prior to the full inflation of intermediate portion 30c. This is done so that deposits D adjacent to intermediate portion 30c are not pushed or "kneaded" toward the first and second ends, where the deposits might break away from interior wall W and form emboli. Because the first and second ends are fully inflated first, such deposits are trapped between the first and second ends. This greatly reduces the formation of emboli. The invention may also use flexible membranes with other inflation strategies, some of which are depicted in FIGS. 10-12. FIG. 10 shows a flexible membrane 62, wherein the end 64 that is nearer the distal end of the catheter fully inflates prior to the remainder of the flexible membrane being fully inflated. FIGS. 11 and 12 depict another inflation strategy in which intermediate segments 66 of flexible membrane 62 are inflated substantially simultaneously with end 64. Intermediate segments 66 are staggered so that deposits D are trapped between the segments as the segments are fully inflated.

Figure 13A:
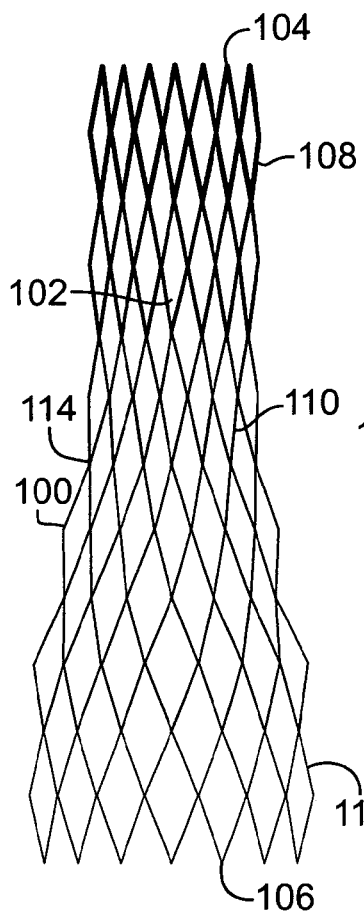
FIG. 13a is a side view of a wire mesh for a stent in accordance with an embodiment of the present invention, the stent shown in an initially dilated configuration.
Figure 13B:
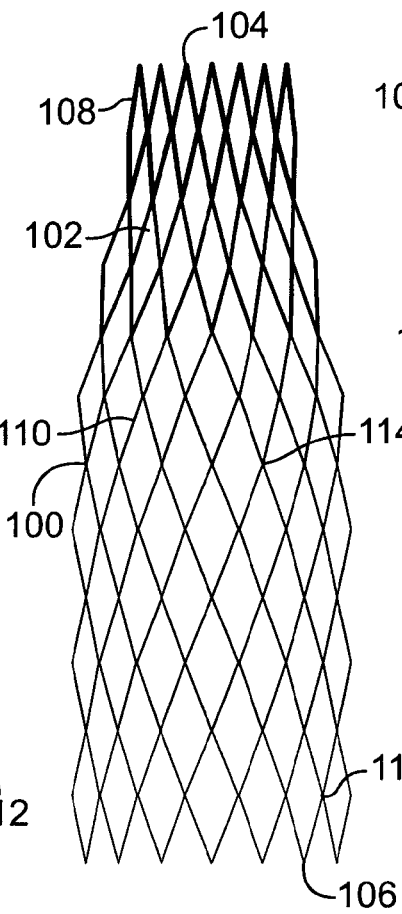
FIG. 13b is a side view of the stent of FIG. 13a, the stent shown in an intermediate dilated configuration.
Figure 13C:
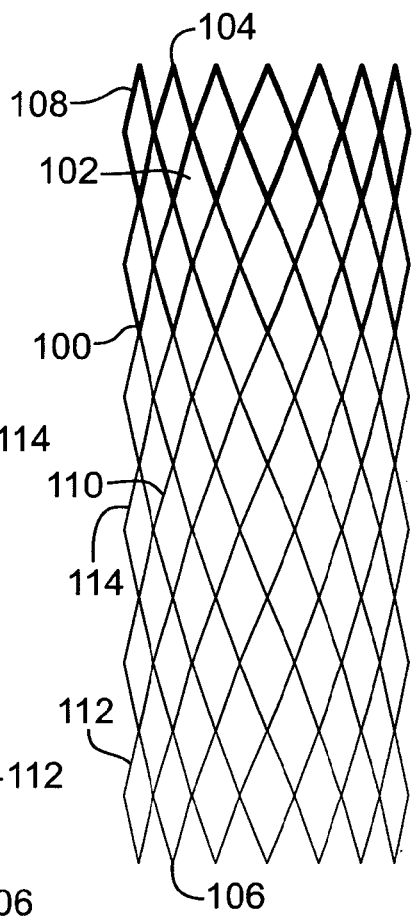
FIG. 13c is a side view of the stent of FIG. 13a, the stent shown in a final, fully dilated configuration.
Figure 14A:
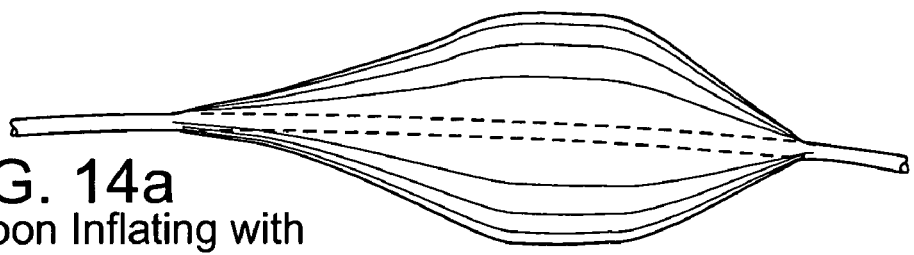
FIG. 14a is a side elevational view of a balloon for use in differentially dilating a stent in accordance with an embodiment of the present invention, the balloon shown in an intermediate dilated configuration.
Figure 14B:
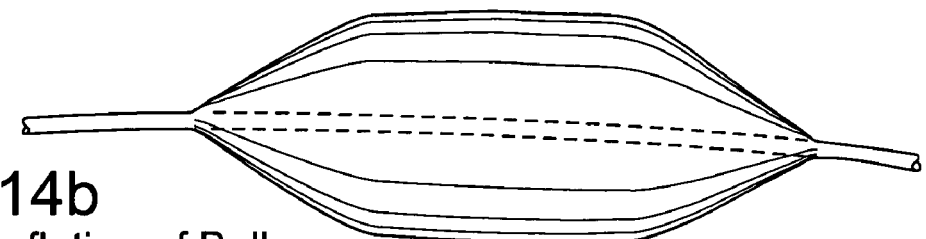
FIG. 14b is a side elevational view of the balloon of FIG. 14a, the balloon shown in a final, fully dilated configuration.
Figure 15A:
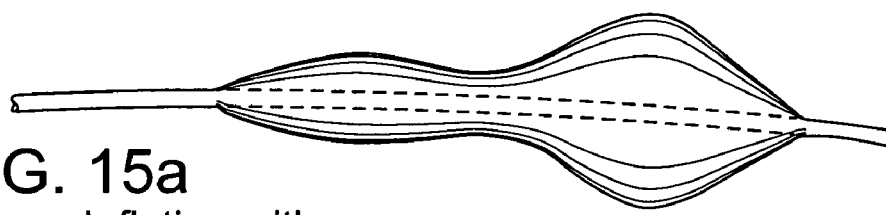
FIG. 15a is a side elevational view of a balloon for use in differentially dilating a stent in accordance with another embodiment of the present invention, the balloon shown in an initially dilated configuration.
Figure 15B:
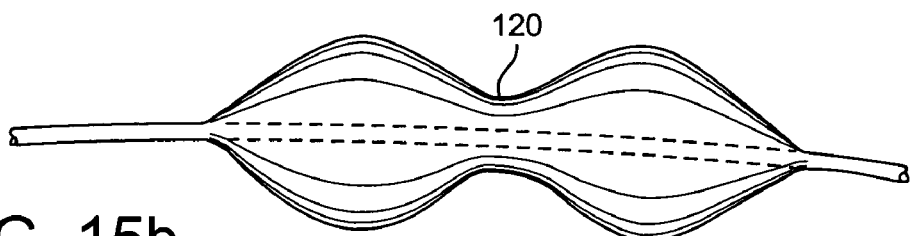
FIG. 15b is a side elevational view of the balloon of FIG. 15a, the balloon shown in an intermediate dilated configuration, or alternatively a septated balloon in a final, fully dilated configuration.
Figure 15C:
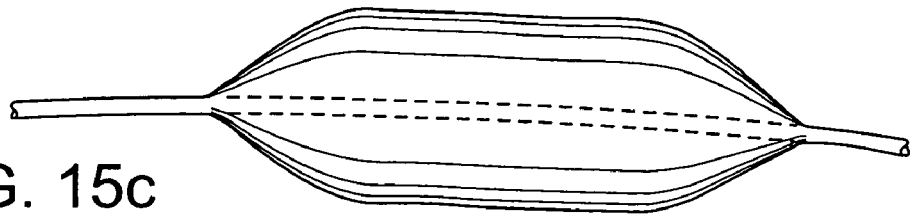
FIG. 15c is a side elevational view of the balloon of FIG. 15a, the balloon shown in a final, fully dilated configuration.

The differential dilation of the stent may be provided by the various configurations for the balloon or by characteristics of the stent itself, either alone or in combination with the balloon configurations just described. An alternative embodiment for a stent for use in the stent delivery system is shown in FIGS. 13a, 13b, and 13c where a mesh layer 100 for a stent 102 is shown. Stent 102 may be uncovered, or it may include flexible coverings, e.g. as described for stents 40 and 80. Stent 102 is in a generally cylindrical shape with first open end 104 and second open end 106. First open end 104 is typically the proximal or upstream end of stent 102 when it is installed in the blood vessel, and second open end 106 is the distal or downstream end. Stent 102 uses a thicker wire 108 to form wire mesh 100 adjacent proximal end 104, an intermediate-sized wire 110 in a central portion 114, and a thinner wire 112 adjacent distal end 106. Additionally, the wire mesh could be formed in a more expandable pattern adjacent distal end 106, and less expandable patterns in the central and proximal portions, which feature might be used with a constant thickness wire, or combined with the varied-thickness wire shown in FIGS. 13a-c. Additionally, wire mesh 102 could be formed using two or more different materials with different inherent resistances to expansion.

The effect of the foregoing characteristics of stent 102 is to provide a stent that expands more readily adjacent distal end 106 as compared to middle portion 114, and middle portion 114 expands more readily than proximal end 104. Alternate configurations for wire mesh 100 may be applied to produce a stent that expands in any style, including those shown in FIGS. 4, 10, 11, and 12, even if the balloon used to expand or dilate the stent is configured to dilate uniformly throughout its length. Additionally, the differentially-dilating balloons described above may be used with stent 102 to enhance the desired effect of differential dilation of the stent, particularly so as to trap any dislodged debris and prevent its downstream flow, either by aspiration or by squeezing it between the stent and the inner lining of the blood vessel.

The embodiments described above show that the invention is effective to permit an operation such as predication or stent installation to be performed on a vessel while ensuring that emboli or other embolism-forming particles created during the operation are removed from the vessel. The invention may also be used with other operations not specifically disclosed herein. The invention may be further varied by using other types of conduit blocking mechanisms, it being understood that the first flexible membranes described above are only exemplary of such blocking mechanisms. The perfusion apparatus may not be included with the embodiments described above, and other ischemia-reducing strategies may be used with the invention. The syringe may have a different capacity. In some circumstances the syringe may be required to have a capacity of 50 cc or more.

Another variation of the invention includes a single flexible membrane that includes a first portion that blocks a conduit when expanded and a second portion that predilates the vessel or installs a stent when expanded. Such an embodiment requires a single lumen and a single controlling fluid that is to be controlled. The selective inflation of the different portions of the flexible membrane may be accomplished by varying the pressure of the controlling fluid or by constructing the portions of the flexible membrane to have different levels of compliance or flexibility.

The flexible membrane with different levels of compliance or flexibility may be used to provide the balloon as shown in FIGS. 3, 10, 11, and 12, and also FIGS. 14a, 14b, 15a, 15b, and 15c, which show similar balloons. The balloon in FIG. 15b may also be understood to represent either an intermediate stage of inflation between that of FIGS. 15a and 15c, or a final stage of inflation for a septated balloon that includes septum 120 that restricts dilation of a central portion of the balloon.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where claims recite "a" or "a first" element or the equivalent thereof, such claims should be understood to include incorporation of one or more such elements, neither requiring nor excluding two or more such elements.

Such claims particularly point out certain combinations and subcombinations that are directed to one of the disclosed inventions and are novel and non-obvious. Inventions embodied in other combinations and subcombinations of features, functions, elements and/or properties may be claimed through amendment of such claims or presentation of new claims in a related application. Such amended or new claims, whether they are directed to a different invention or directed to the same invention, whether different, broader, narrower or equal in scope to the original claims, are also included within the subject matter of the inventions of the present disclosure.

I claim:

1. A stent configured for insertion in a human blood vessel, the stent comprising:
   a body with an inner layer providing a first flexible covering;
   an outer layer providing a second flexible covering;
   a middle wire mesh layer between the inner and outer layers, the wire mesh layer providing a compressible, self-expanding structure; and
   at least one of the inner and outer layers are provided with a radiopaque portion adjacent at least one of the first and second ends.

2. The stent of claim 1 wherein the inner and outer layers of the stent include PTFE.

3. The stent of claim 1 wherein the wire mesh layer includes nitinol.

4. The stent of claim 1 wherein the middle layer defines first and second ends and the middle layer includes a radiopaque portion adjacent at least one of the ends.

5. The stent of claim 1 wherein the inner and outer layers each define first and second ends, and further wherein the inner and outer layers are sized and aligned with their ends extending beyond the ends of the middle layer.

6. The stent of claim 1 wherein the inner and outer layers each define an end-to-end length and the inner and outer layers are sized to be substantially equal in length.

7. The stent of claim 6 wherein the middle layer defines an end-to-end length that is less than the end-to-end lengths of the inner and outer layers.

8. The stent of claim 1 wherein the inner and outer layers are sealed together adjacent the first and second ends, encasing and fixing in place the middle layer.

9. The stent of claim 7 wherein the middle layer length is 0.5 mm less than at least one of the inner and outer layers length.

10. The stent of claim 1 wherein the middle layer includes a radiopaque portion adjacent at least one of the ends, the combination of the radiopaque portion of the middle layer and the radiopaque portion of the inner or outer layer providing an X-ray indication of whether the middle layer has expanded beyond the ends of the inner and outer layers.

* * * * *